United States Patent [19]

Harvie

[11] Patent Number: 5,750,776
[45] Date of Patent: May 12, 1998

[54] PRODUCTION OF DICARBOXYLIC ACIDS OR ESTERS THEREOF

[75] Inventor: James Lumsden Harvie, Middlesbrough, United Kingdom

[73] Assignee: Imperial Chemical Industries PLC, Great Britain

[21] Appl. No.: 564,227

[22] PCT Filed: Jun. 29, 1994

[86] PCT No.: PCT/GB94/01411

§ 371 Date: Dec. 18, 1995

§ 102(e) Date: Dec. 18, 1995

[87] PCT Pub. No.: WO95/01954

PCT Pub. Date: Jan. 19, 1995

[30] Foreign Application Priority Data

Jul. 5, 1993 [GB] United Kingdom ............... 9313892
Jul. 5, 1993 [GB] United Kingdom ............... 9313896

[51] Int. Cl.$^6$ ................................................. C07C 51/487
[52] U.S. Cl. ................................................. 562/483; 560/98
[58] Field of Search ................................................. 562/483; 560/98

[56] References Cited

U.S. PATENT DOCUMENTS

| | | |
|---|---|---|
| 3,120,561 | 2/1964 | Chambret . |
| 3,257,335 | 6/1966 | Barnard et al. . |
| 3,703,488 | 11/1972 | Morton . |
| 3,884,850 | 5/1975 | Ostrowski . |
| 4,578,510 | 3/1986 | Doerr . |
| 4,605,762 | 8/1986 | Mandoki . |
| 4,620,032 | 10/1986 | Doerr . |
| 5,223,544 | 6/1993 | Burkett et al. . |

FOREIGN PATENT DOCUMENTS

| | | |
|---|---|---|
| 550979 | 12/1992 | European Pat. Off. . |
| 729187 | 12/1966 | Italy . |
| 822834 | 11/1956 | United Kingdom . |
| WO 93/23465 | 11/1993 | WIPO . |

Primary Examiner—Samuel Barts

[57] ABSTRACT

Dicarboxylic acids or esters thereof are recovered from solid phase polyester materials, such as post-consumer products and factory scrap, by initially subjecting the polyester to a glycolysis reaction (in one or more stages) to produce a liquid phase medium containing depolymerisation products. The liquid phase medium is then contacted with aqueous medium or alcohol in one or ore stages to produce the dicarboxylic acid or an ester thereof together with glycol.

21 Claims, No Drawings

PRODUCTION OF DICARBOXYLIC ACIDS OR ESTERS THEREOF

This application is a 371 of PCT/GB94/01411 filed Jun. 29, 1994.

This invention relates to the production of dicarboxylic acids or esters thereof The invention is particularly concerned with the production of such acids by means of the depolymerisation of polyesters, particularly condensation polyesters such as polyalkylene terephthalates and polyalkylene naphthalates, in order to recover dicarboxylic acids.

It is known that terephthalic acid which is suitable for polymerisation with alkylene glycols either directly or after purification may be obtained by the hydrolysis of waste polyalkylene terephthalate.

GB-A-2123403 discloses a continuous procedure for obtaining terephthalic acid from PET waste in which the PET waste is heated in water and in which process the presence of decolourising carbon in the water is essential. Additionally, this procedure utilises sufficient water, and is operated at such a temperature, that the terephthalic acid product dissolves in the water as it is produced to form an aqueous solution of terephthalic acid, there being substantially no terephthalic acid in the solid phase, which solution is subsequently filtered to remove the carbon. The terephthalic acid is then crystallised from the filtrate.

It is also known from East German Patent No. 14854 to produce terephthalic acid by hydrolysis of PET. In this case, the teaching also appears to be directed towards producing the terephthalic acid product in solution at the reaction conditions employed. The disclosure refers to filtering the hot reaction solution under pressure using a filter which can trap both colouring and mechanical impurities. The hot solution is thereafter cooled to crystallise the terephthalic acid which is then isolated and dried.

U.S. Pat. No. 5,095,145 is likewise concerned with effecting depolymerisation of waste PET products by depolymerisation thereof in an aqueous mixture at a temperature within the range 430° to 600° F. to produce an aqueous crude terephthalic acid solution which is thereafter processed further.

U.S. Pat. No. 3,257,335 discloses a two stage process for depolymerising polyesters, particularly polyethylene terephthalate, to produce low molecular weight terephthalic esters of ethylene glycol in ethylene glycol solutions which can be stored as a liquid at reduced temperatures for extended periods of time without solidification or excessive degradation. The process disclosed comprises dissolving waste polyester in monomer at atmospheric pressure and at a temperature greater than the boiling point of ethylene glycol but less that the boiling point of the mixture, pumping the resulting solution together with fresh ethylene glycol into a tubular reactor at a higher temperature than the dissolver and pressure in excess of the vapour pressure of ethylene glycol at that temperature, recycling part of the reaction product to the dissolver and removing the remainder for storage.

In our prior European Patent Application No. 92 311421.9, there is disclosed a process for the production of terephthalic acid from polyalkylene terephthalate by hydrolysing the terephthalate in such a way that, at the reaction temperature, at least part (preferably a major part) of the terephthalic acid is produced in the solid phase. This provides benefits in terms of the extent of post-reaction crystallisation necessary to recover the terephthalic acid and the extent of water removal necessary to effect recovery of glycol produced in the reaction. The hydrolysis may be carried out in two stages and glycol may be present in the reaction mixture so as to increase the proportion of glycol present relative to water thereby simplifying the recovery of glycol following the reaction.

The present invention seeks to provide an improved process for the depolymerisation of polyesters.

According to a first aspect of the present invention there is provided a process for effecting depolymerisation of solid phase polyesters in order to recover dicarboxylic acids and alkylene diols therefrom, comprising:

(a) reacting the solid phase polyester with a diol at a reaction temperature which is in excess of 10° C. above the boiling point of the diol to produce a liquid phase medium containing lower molecular weight depolymerisation products; and (b) reacting the resulting liquid phase medium with a medium comprising water and/or an aliphatic monohydric alcohol to effect further depolymerisation of said low molecular weight depolymerisation products into dicarboxylic acid or an ester thereof.

According to another aspect of the invention a process for effecting depolymerisation of solid phase polyesters in order to recover dicarboxylic acids and alkylene diols therefrom, comprises:

(a) reacting the solid phase polyester with a diol at a reaction temperature of at least 210° C. to produce a liquid phase medium containing lower molecular weight depolymerisation products; and (b) reacting the resulting liquid phase medium with a medium comprising water and/or an aliphatic monohydric alcohol to effect further depolymerisation of said low molecular weight depolymerisation products into dicarboxylic acid or an ester thereof Step (b) may be carried out in one or more stages, as disclosed in our co-pending UK Patent Application No. 93 13892.3 of even date, the entire disclosure of which is incorporated herein by reference.

The invention has application for example to polyesters such as polyalkylene terephthalates in which the dicarboxylic acid or ester comprises terephthalic acid or a terephthalic ester (eg dimethyl terephthalate), and polyalkylene naphthalates in which the dicarboxylicacid or ester comprises naphthylene 2,6 dicarboxylic acid or an ester thereof.

The liquid phase medium following the reaction of step (a) will also often contain residual diol, particularly where an excess of the diol is used in the reaction.

A feature of the invention resides in reacting the polyester with an alkylene diol prior to the hydrolysis or alcoholysis reaction. The latter reaction often requires elevated pressure which gives rise to problems, especially in continuous processes, from the standpoint of introducing the solid phase polyester into a reactor under elevated pressure and temperature conditions since solid phase polyester (eg post-consumer and factory scrap) is commonly in a form which is not readily amenable to slurrying and pumping. Also, solid phase polyester often has a relatively low bulk density and the amount of aqueous medium required to totally immerse the polyester is significantly greater than that needed on a weight for weight basis to treat that amount of polyester. By carrying out step (a) in order to produce liquid phase medium, the problem of introducing a solid phase reactant at atmospheric pressure into elevated pressure conditions is obviated since it is a relatively simple matter to pump a liquid phase medium into a reactor operating under high pressure conditions. Also, the amount of water can be substantially reduced compared with that required to totally immerse low bulk density solid phase polyester. Because diols are much less volatile than water, the reaction of step (a) can be carried out at least initially at much lower pressure than is necessary for hydrolysis.

Another advantage stemming from step (a) is that the solid phase polyester can be fed substantially continuously into the reaction of step (a), whereas continuous feed of solid phase polyester directly into a hydrolysis or alcoholysis reactor operating under elevated temperature and pressure conditions is technically very difficult.

A further advantage conferred by step (a), as opposed to carrying out the hydrolysis or alcoholysis of solid phase polyester directly, is that various treatments of the resulting liquid phase medium can be carried out prior to carrying out step (b). In particular, it becomes feasible to subject the liquid phase medium to a separation process, eg filtration, to remove undesirable insoluble particulate impurities, such as aluminium, paper, polystyrene, polyolefines and PVC, commonly present in washed polyesters, such as post-consumer and factory scrap polyesters. Also, by suitable management of the liquid phase medium, extraction of impurities by means of contact with for instance activated carbon (eg for decolourising the liquid phase medium) or an ion exchange resin may be effected in order to remove contaminants such as chloride or ionic catalyst residues present in the liquefied polyester.

Typically, step (a) will be carried out at elevated temperature in excess of temperatures at which use of ion exchange resins can normally be entertained; thus, for instance, prior to extraction of contaminants using means such as an ion exchange resin, the liquid phase medium may be cooled to a temperature within a range allowing the use of such extraction means. Water or other suitable polar solvent may be added to the liquid phase medium to assist in solubilising the lower weight depolymerisation products at lower temperatures and/or to assist in ionising impurities to facilitate removal of soluble impurities.

Step (a) may be carried out in two stages, a first low pressure stage in which the reaction with the diol serves to produce said lower molecular weight depolymerisation products and a second higher pressure stage in which the reaction with the diol proceeds further in order to produce even lower molecular weight depolymerisation products. The second stage may involve the introduction of additional diol (which is preferably the same as that used in the first stage).

The second stage confers the advantage that the production of even lower depolymerisation products permits the liquid phase to be cooled without solidifying to temperatures lower than is possible with longer chain depolymerisation products. It is therefore more feasible to cool the temperature of the liquid phase medium to within a range compatible with the use of ion exchange resins. Cooling may also be desirable where other filtration/removal techniques are used, eg activated carbon, semi-permeable membranes, etc.

A further advantage of being able to cool to relatively low temperatures is that the liquid product can be stored as such without degrading significantly.

The first stage is conveniently carried out in a continuous fashion with solid phase polyester and diol being introduced to the reaction concurrently with removal of said liquid phase medium. Thus, in steady state operation of the process, liquid phase medium may be continuously withdrawn from the first stage of the reaction and may be pumped continuously into the higher pressure second stage.

Advantageously, particularly in terms of aiding eventual separation and recovery thereof, the diol used in step (a), and where the context admits in each stage of step (a), is the same as the diol which is derived from the polyester in step (b). For instance, in the case where the starting polyester is constituted by polyethylene terephthalate, the diol used in step (a) is preferably monoethylene glycol. In some instances, step (a) may be carried out using a mixture of different diols of which one will preferably be the same as that derived from the polyester in step (b).

Some polyesters are produced by the reaction of a polycarboxylic acid with a mixture of diols. Where the polyester to be processed in accordance with the invention is of this type, the diol used in the polyester/diol reaction is preferably the same as the diol which formed the major component of the diol mixture originally used in the production of the polyester.

Where an aqueous medium is used in step (b), the final product will be a dicarboxylic acid. If a monohydric alcohol is used, the product will be the diester of the dicarboxylic acid. In both cases, glycol will also be produced in the reaction.

Where step (b) is carried out using aqueous medium as opposed to monohydric alcohol, preferably step (b) is carried out in such a way that, under the prevailing reaction conditions, at least a major part (more preferably at least 70%, and most preferably at least 80%, even as much as 90% or more) of the dicarboxylic acid is produced in the solid phase. In this event, it may be necessary to reduce the diol content of the liquid phase medium prior to step (b). It will in any event usually be desirable to reduce the amount of diol present in the liquid phase medium following step (a), whether conducted in one or more stages, since the amount of water then needed in step (b) may be less.

A number of advantages may be secured by effecting the reaction of step (b) in such a way as to produce a substantial part of the dicarboxylic acid in the solid phase rather than being completely dissolved in the reaction medium. Thus, less recrystallisation is necessary to recover the dicarboxylic acid from the reaction medium as compared with the processes of the prior art. Also to obtain a substantial amount of the dicarboxylic acid in the solid phase under the reaction conditions requires a relatively large ratio of polyester to water in the mixture prior to heating and, as a result, a relatively concentrated solution of diol in the reaction liquor is obtained following the hydrolysis reaction which leads to correspondingly less water to remove in order to recover the diol. The costs of such recovery are thus reduced.

Further, by ensuring that at least part of the dicarboxylic acid is produced in the solid phase during the course of the hydrolysis reaction of step (b), the reaction equilibrium can be shifted in the desired direction thereby enhancing recovery of the dicarboxylic acid.

The solid phase polyester to be treated in accordance with the process of the invention may be in any suitable form although it is preferred that the polyester is in the form of particles such as granules, powder or flakes, derived by the comminution or other mechanical breakdown of manufactured articles consisting of or containing polyester. For instance, in the case of polyethylene terephthalate (PET), bottles provide a major source of PET suitable for recycling to produce terephthalic acid although it may be desirable to separate the PET from any other plastics materials contained in the bottles such as polyvinylchloride (PVC) prior to hydrolysis. Other sources of PET include fibres and film.

Although it is preferred to comminute polyester products such as bottles into particles, flakes or other finely divided form, we do not exclude the possibility of using the process of the invention to treat finished polyester products in order to recover the dicarboxylic acid or ester thereof.

Where step (b) comprises a hydrolysis reaction, suitably the aqueous medium employed is demineralised water thus reducing the possibility of competing reactions reducing the yield of terephthalic acid; however, other polar solvents such as diols, especially an alkylene diol such as ethylene glycol, may be present if desired as disclosed in our prior European Patent Application No. 92 311421.9.

Where step (b) comprises an alcoholysis reaction, the alcohol used will usually be methanol and, in the case of polyethylene terephthalate, the product will be dimethyl terephthalate and glycol.

In one embodiment of the invention as applied to the depolymerisation of PET in order to recover terephthalic acid and ethylene glycol, the solid phase polyester (after being comminuted to a suitable particle size) is subjected to a glycolysis reaction at low pressure (atmospheric or near-atmospheric) but elevated temperature sufficient to produce a liquid phase medium containing the glycol and primarily low molecular weight depolymerisation products (herein referred to as oligomers) although some higher molecular weight depolymerisation products (in excess of 20 repeat units) may be present, possibly together with some unreacted polyester.

The glycolysis reaction is conveniently carried out in the substantial absence of molecular oxygen at atmospheric pressure or near atmospheric pressure (eg up to several pounds/inch$^2$ in excess of atmospheric pressure). The glycolysis reaction preferably employs the same diol as that used in the production of the polyester, eg ethylene glycol, and is operated at a temperature of at least 210° C., more preferably 210° to 280° C. and most preferably 210° to 230° C.

The low pressure glycolysis reaction is preferably carried out on a continuous basis with solid phase PET and ethylene glycol being supplied to the reaction concurrently with removal of liquid phase medium from the reaction and is carried out at a temperature which is at least 10° C. in excess of the normal boiling point (about 196° C.) of the ethylene glycol used since the depolymerisation products/oligomers generated during the course of the reaction tend to have high boiling points thereby reducing the liquid vapour pressure and allowing the reaction to proceed without boiling off substantial quantities of the glycol. By carrying out the reaction at an elevated temperature compared with the normal boiling point of the glycol, the reaction may proceed more rapidly.

Liquid phase medium withdrawn from the low pressure glycolysis reaction is conveniently filtered at this stage using some form of mechanical filter to screen out particulates such as aluminium, lumps of PVC, paper etc commonly present in scrap/post-consumer PET. The liquid phase medium may then be optionally treated to remove other impurities, for instance by contact of the medium with activated carbon and/or an ion exchange resin, in which case cooling of the liquid phase medium is effected prior to such contact. Thus where, for example, a technique involving contact with a material such as an ion exchange resin is employed, requiring the liquid phase medium to be cooled to a temperature compatible with the material employed in such technique, the liquid phase medium is typically cooled to a temperature within the range 50° to 130° C. (preferably 70° to 100° C.) prior to treatment by such technique. The cooling may be effected either prior to filtration of the soluble impurities (eg aluminium, paper, PVC etc) from the liquid phase medium or subsequent to such filtration.

Optionally the liquid phase medium containing glycol and low molecular weight PET depolymerisation products is subjected to a second more severe glycolysis reaction at increased pressure (if necessary with added glycol) to break down the PET further, preferably to form hydroxy ethylene terepthalate compounds of the form:

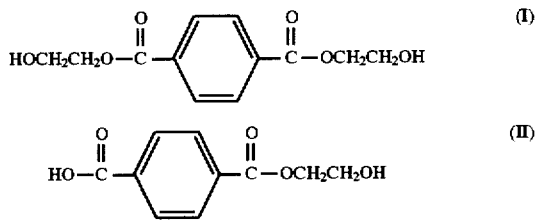

(which may be termed bis-hydroxy ethylene terephthalate (BHET) and mono-hydroxy ethylene terephthalate (MHET) respectively). Usually the diglycol depolymerisation products (such as BHET) will be the predominant components and there may be little if any depolymerisation products with acid groups (such as MHET) present. Acid end groups are usually formed as a consequence of water being introduced into the glycolysis reactor (eg as a result of using damp glycol or PET). The more severe glycolysis reaction may be carried out using at a temperature within the range 180° to 260° C. (preferably 210° to 230° C.) and a pressure in the range 1 to 10 bara (preferably 2 to 5 bara).

The liquid phase medium derived from the first glycolysis stage may be pumped continuously from the first stage to the second glycolysis stage.

Where two stages of glycolysis are used, both stages are conveniently carried out in the substantial absence of molecular oxygen. Also, the filtration and other treatment processes may be carried out at any suitable point in the process, eg before or after the second stage. Typically, the filtration of insoluble contaminants may be effected at a point intermediate the two stages by passage of the liquid phase medium through a metal gauze or the like and the extraction of impurities using activated carbon, ion exchange resins or the like may be carried out after the second stage, following cooling and pressure let-down of the liquid phase medium if necessary.

Following glycolysis and optional treatments such as impurity filtration/extraction and glycol reduction, the liquid phase medium may be cooled and collected for storage in a buffer tank or tanks.

Prior to hydrolysis of the liquid phase medium (following glycolysis reaction in one or two stages), the medium is conveniently processed to reduce its glycol content, eg by flashing in a suitable vessel, thereby requiring less water in the subsequent aqueous hydrolysis step to generate any desired number of acid end groups. The glycol content will comprise both glycol added as reactant (in both glycolysis stages where applicable) and that generated in the course of the glycolysis and the reduction process will usually result in removal of a major part of the glycol. The removal of glycol, eg by flashing, is preferably effected, eg at low pressure, to avoid excessive rise in viscosity and repolymerisation of the hydroxy ethylene terephthalate compound (s).

The hydrolysis reaction is typically carried out in the absence of added acids or alkalis. A desirable feature of the hydrolysis reaction, especially if carried out in a single stage, is that it should be carried out under conditions which ensure that a substantial proportion of the terephthalic acid is produced in the solid phase during the course of the reaction; ideally as little as possible of the terephthalic acid produced under the reaction conditions should be in solution. In most cases, the reaction will be carried out so as that at least 70%, preferably at least 80%, even in excess of 90% of the terephthalic acid is produced in the solid phase. This can be achieved by employing comparatively low reaction temperature for the hydrolysis, certainly less than 300° C. (typically in the range 190° to 240° C. and preferably about 200° to about 220° C.) and by using small quantities of water to secure high conversion to terephthalic acid. Hydrolysis at temperatures lower than 190° C. may be employed if desired; however in order to secure a terephthalic acid yield similar to that obtained at higher temperatures, the reaction time must be increased significantly.

The formation of terephthalic acid in the solid phase during the hydrolysis reaction results in a relatively small particle size and also allows particle size to be controlled at this stage. Thus, the process of the present invention may include controlling the nature of particle formation during the hydrolysis reaction. More specifically, particle formation is preferably controlled in such a way that the particles of solid phase terephthalic acid forming during the hydrolysis reaction are of rounded shape, desirably such that at least 90% of the particles of the recovered solid phase terephthalic acid are sufficiently small to pass through a sieve having a grid size 2 mm, preferably 1 mm, more preferably 800 microns, and especially 500 microns square. Thus, by controlling the particle size during the hydrolysis reaction, it becomes possible to achieve a desired particle size and distribution consistent with the requirements imposed by subsequent processing of the terephthalic acid product, without the necessity for a separate processing vessel (eg crystalliser) for treating the terephthalic acid in order to obtain the desired particle size and distribution. Various ways of controlling particle size can be contemplated such as control of the temperature gradient within the reaction vessel and/or the provision of surfaces which promote formation of the desired particle shape and size. One particularly effective control technique is to effect agitation of the reaction mixture during hydrolysis, for example by means of stirring. Agitation may be continued after the hydrolysis reaction has been completed and during cooling of the reaction mixture so as to promote crystallisation of terephthalic acid which has remained in solution in the form of rounded particles (as opposed to needle-shaped particles which may be up to 1 cm or above in length as tends to happen if the solution is allowed to cool naturally).

Preferably therefore, the reaction mixture is suitably agitated during heating. By suitably controlling particle size formation from the reaction mixture, for instance by agitation of the reaction mixture, it is possible to secure that at least 90% of terephthalic particles recovered are of rounded shape capable of passing a sieve having a square grid size of 2 mm (more preferably 1 mm and even more preferably 500 microns) as opposed to needle-shaped particles, which is advantageous when the particles are subsequently slurried with alkylene glycol in the course of PET production since particle packing density is of importance in this respect.

Desirably, the hydrolysis is conducted at a temperature and for sufficient time to provide a yield of terephthalic acid of at least 70%, preferably at least 90%, especially at least 95% for example at least 98 mole % based on the moles of terephthalate units in the polyalkylene terephthalate.

The pressure at which hydrolysis may be carried out is usually determined by the temperature of the reaction in a closed vessel but is preferably conducted at elevated pressure.

Conveniently, in order to avoid undesirable oxidation, hydrolysis is carried out in the absence of molecular oxygen and suitably under a blanket of an inert gas, for example nitrogen.

The hydrolysis is suitably carried out for sufficient time to provide the desired degree of hydrolysis and is preferably up to 5 hours, more preferably 10 minutes to 3 hours and especially 30 minutes to 2 hours. The period over which hydrolysis is carried out may also depend on the particular form of polyalkylene terephthalate to be hydrolysed.

The terephthalic acid produced in the solid phase may be separated from the aqueous medium conventionally for example by filtration to provide terephthalic acid which is substantially free of impurities. Impurities which may be present during the hydrolysis include organic impurities such as comonomers present in the PET and adventitious contaminants present on the PET, and metal residues contained in the PET which may be for example residues derived from the polymerisation catalyst employed in the production of the polyalkylene terephthalate. Any soluble metal impurities present may be separated from the terephthalic acid by employing a hot filtration in which the terephthalic acid is retained by the filter and metal impurities are suitably carried through the filter into the filtrate. Typically said hot filtration is carried out at a temperature of at least 50° C., a suitable range being from about 60° to about 100° C.

Following the hot filtration step, the recovered terephthalic acid is preferably subjected to at least one hot wash followed by filtration. For instance, the recovered terephthalic acid may be reslurried in fresh water and heated to effect a hot wash. Glycol may also be incorporated in the hot wash to facilitate stripping from the recovered terephthalic acid oligomers formed during the hydrolysis reaction.

The hot washed terephthalic acid/water is then subjected to filtration to separate the terephthalic acid. Hot washing in this manner has been found to enhance removal of impurities, especially yellow colour formers.

Hot washing is typically carried out at a temperature of at least 50° C., a suitable range being from about 60° C. to about 100° C.

After hydrolysis is complete, the terephthalic acid is recovered by suitable filtration and drying (if required—ie. drying may not be necessary if the recovered terephthalic acid is to be blended with terephthalic acid derived from other sources such as the liquid phase oxidation of p-xylene). Advantageously the recovery of the terephthalic acid includes one or more washing steps, using the same or different wash liquors for each step where multiple washing steps are employed, to remove particular species of organic impurities (for instance to ensure food contact approval), especially water insoluble impurities, to reduce the water content and improve the product colour. The washing step (s), or any one or more of them, may be carried out using heated wash liquor.

Filtration of the terephthalic acid is conveniently carried out by means of a belt filter. Following filtration the terephthalic acid filter cake may be transported on the belt filter through one or more washing stages in which it is washed with a wash liquor or more than one wash liquor, the wash liquor(s) being drawn through the belt filter to leave a washed deposit which may then be dried in any suitable manner. Acetone is a convenient washing liquor since it may serve all of the purposes mentioned above, ie removal of organic species, improvement of product colour and drying.

The terephthalic acid recovered from the process may be re-used in the production of polyesters, if necessary after the terephthalic acid has been subjected to a purification process such as that conventionally employed in the production of pure terephthalic acid. Thus, for example, the recovered terephthalic acid, optionally together with terephthalic acid derived from other sources (for instance crude terephthalic acid produced by the liquid phase oxidation of p-xylene) may be dissolved to form an aqueous solution which is then contacted with hydrogen in the presence of a noble metal catalyst (eg palladium and/or platinum supported on an inert support such as carbon) at a temperature within the range 250° to 350° C. and a hydrogen partial pressure of 5 to 25 bara. Alternatively, the terephthalic acid may be purified by recrystallisation from solution.

It will be appreciated that, whilst the invention has been described hereinbefore with reference to the processing of PET to recover terephthalic acid and glycol, similar process steps may be employed in the case of other condensation polyesters such as polyethylene naphthalate.

The invention will now be illustrated further without limitation with reference to the following Example.

EXAMPLE 300 g monoethylene glycol and 700 g post-consumer PET flake was added to an insulated glass vessel fitted with a nitrogen purge (allowing the reaction to be carried out in an inert gas atmosphere), a thermocouple and a condenser. The vessel contents were heated slowly to 226° C. and held at this temperature under atmospheric pressure for 4 hours. 800 g of product were removed by filtering the vessel contents through a glass wool plug inserted into an outlet at the base of the reactor. The plug was found to hold back a substantial amount of contaminants (such as portions of bottle tops, etc). The filtered liquid was introduced together with 871 g of distilled water into an autoclave and heated to 150° C. for 2.5 hours. On cooling, a white precipitate was found to comprise 95.4% by weight terephthalic acid.

As illustrated in the above Example and the following Table 1, the glycolysis stage (or the first glycolysis stage, where more than one is employed), is preferably carried out using a PET to diol w/w ratio of at least unity, more preferably greater than unity. Moreover, the PET and diol additions are preferably made progressively and in proportions (with accompanying removal of liquid phase medium from the reaction) such that the reaction temperature is maintained substantially constant at temperature which is in excess of 10° C. above the boiling point of the diol. The effect of PET/diol ratios on molecular weights is further illustrated in Table 1 which gives the molecular weight attained a given time after the completing the progressive addition of the diol (MEG-monoethylene glycol in this case) and/or PET, the PET being in the form of commercially available PET scrap (obtainable from suppliers such as REKO BV of Geleen, Holland and Reprise Technologies of Bollington, England). Generally the reaction would have been in progress for longer than the specified time since, as mentioned above, the PET and glycol are added in such a way as to maintain the reaction temperature and the boiling point of the reaction mixture substantially constant (PET addition raises the boiling point as it uses up more glycol whilst glycol addition lowers the boiling point).

TABLE 1

| Run No. | Final temp °C. | Time mins | PET/MEG w/w ratio | Mw | Mn |
|---|---|---|---|---|---|
| 1 | 205 | 200 | 0.71 | 318 | 216 |
| 2 | 212 | 500 | 1.7 | 564 | 415 |
| 3 | 238 | 30 | 2.6 | 615 | 458 |
| 4 | 225 | 45 | 2.8 | 591 | 432 |
| 5 | 222 | 45 | 3.4 | 641 | 465 |

TABLE 1-continued

| Run No. | Final temp °C. | Time mins | PET/MEG w/w ratio | Mw | Mn |
|---|---|---|---|---|---|
| 6 | 225 | 45 | 4 | 628 | 450 |
| 7 | 226 | 20 | 4.2 | 944 | 605 |
| 8 | 232 | 15 | 4.6 | 875 | 601 |
| 9 | 225 | 30 | 7 | 600 | 434 |

These results indicate that the operating temperature at atmospheric pressure depends on residence time in the reactor as well as the feed ratio of PET to glycol. In order to maintain a temperature of at least 210° C. using ethylene glycol, the feed ratio should be at least 1 PET:IMEG by weight. Higher proportions of PET relative to MEG can be used to reduce residence time in the reactor.

Where a second glycolysis stage is employed, the ratio of diol to PET also plays an important role, as illustrated in Table 2 which shows the clouding point and molecular weights for different MEG/PET w/w ratios, where the clouding point corresponds to the temperature at which a solution containing the depolymerisation products becomes cloudy as it is cooled at a rate of about 1° C./min as a result of the solubility of the oligomers decreasing to the point where they are not entirely soluble. In this case, diol to PET w/w ratios in excess of unity are preferred so that substantially all of the depolymerisation products are in solution at temperatures compatible with processes such as filtration thereby avoiding deposition of the depolymerisation products in or on the filter medium. In Table 2, each run involved carrying out further glycolysis of pre-glycolised PET (the specified MEG:PET ratios being based on the starting amount of PET, ie before primary glycolysis) at a reaction temperature of 220° C. and then allowing the resulting mixture to reach equilibrium during a period of 2 hours at that temperature. The PET used comprised commercially available scrap PET.

TABLE 2

| Run No. | Mw | Mn | MEG:PET w/w ratio | Clearing Temp °C. |
|---|---|---|---|---|
| 1 | 318 | 286 | 1.4 | 130 |
| 2 | 333 | 291 | 2.1 | 110 |
| 3 | 293 | 267 | 2.2 | 70 |
| 4 | 289 | 263 | 2.2 | 80 |
| 5 | 354 | 324 | 2.2 | 80 |
| 6 | 307 | 286 | 2.2 | 80 |
| 7 | 288 | 269 | 2.2 | 70 |
| 8 | 283 | 260 | 2.4 | 80 |

I claim:

1. A process for effecting depolymerisation of solid phase polyesters in order to recover dicarboxylic acids and alkylene diols therefrom, comprising:

(a) in a first zone reacting the solid phase polyester with a diol at a reaction temperature which is in excess of 10° C. above the boiling point of the diol to produce a liquid phase medium containing lower molecular weight depolymerisation products;

b) transferring the liquid phase medium from said first zone to a second zone in which elevated pressure conditions prevail; and c) in said second zone reacting the lower molecular weight depolymerisation products from step a) with a medium comprising water to effect further depolymerisation of said low molecular weight depolymerisation products into dicarboxylic acid, in such a way that, under the prevailing reaction conditions, at least a major part of the dicarboxylic acid is produced in the solid phase.

2. A process as claimed in claim 1 in which step (a) is carried out at a reaction temperature of at least 210° C.

3. A process for effecting depolymerisation of solid phase polyesters in order to recover dicarboxylic acids and alkylene diols therefrom, comprising:
 (a) in a first zone reacting the solid phase polyester with a diol in more than one stage to produce a liquid phase medium containing lower molecular weight depolymerisation products;
 b) transferring the liquid phase medium from said first zone to a second zone in which elevated pressure conditions prevail; and
 c) in said second zone reacting the resulting liquid phase medium with a medium comprising water to effect further depolymerisation of said low molecular weight depolymerisation products into dicarboxylic acid in such a way that, under the prevailing reaction conditions, at least a major part of the dicarboxylic acid is produced in the solid phase.

4. A process as claimed in claim 1 in which the diol is the same diol as that used to produce the polyester.

5. A process as claimed in claim 4 in which the diol comprises ethylene glycol.

6. A process as claimed in claim 1, 2 or 3 in which step (c) is carried out in more than one stage.

7. A process as claimed in claim 1 in which said liquid phase medium is subjected to at least one separation or extraction process prior to step (b) to separate therefrom at least some impurities that may be present.

8. A process as claimed in claim 7 in which the liquid phase medium is cooled following step (a) and the cooled liquid phase medium is subjected to a separation/extraction process.

9. A process as claimed in claim 7 in which the separation/extraction process to which the cooled liquid phase medium is subjected comprises contacting the liquid phase medium with an ion exchange resin.

10. A process as claimed in claim 1 or 2 in which step (a) is carried out in at least two stages.

11. A process as claimed in claim 10 in which step (a) is carried out in two stages; a first low pressure stage in which the reaction with the diol serves to produce said lower molecular weight depolymerization products and a second higher pressure stage in which the reaction with the diol proceeds further in order to produce even lower molecular weight depolymerization products.

12. A process as claimed in claim 11 in which the second stage involves the introduction of additional diol which is the same as that used in the first stage.

13. A process as claimed in claim 1 or 3 in which step (a) or the first stage thereof is carried out in such a way that the polyester and diol are introduced to the reaction so as to main a reaction temperature which is more than 10° C. in excess of the boiling point of the diol.

14. A process as claimed in claim 1 or 3 in which step (a) or the first stage thereof is carried out in a continuous fashion with solid phase polyester being introduced to the reaction concurrently with removal of said liquid phase medium.

15. A process as claimed in claim 1 or 3 in which the amount of diol present in the liquid phase medium following step (a) is reduced prior to carrying out step (c).

16. A process as claimed in claim 1 or 3 in which step (a) or the first stage thereof is carried out in the substantial absence of molecular oxygen.

17. A process as claimed in claim 1 or 3 in which step (a) or the first stage thereof is carried out in the substantial absence of molecular oxygen.

18. A process as claimed in claim 1 or 3 in which step (c) or the first stage thereof is carried out in the substantial absence of molecular oxygen.

19. A process as claimed in claim 1 or 3 in which step (c) is carried out in the absence of any added acids.

20. A process as claimed in claim 1 or 3 comprising recovering the dicarboxylic acid following said hydrolysis reaction and contacting the same with acetone.

21. A process for effecting depolymerization of solid phase polyesters in order to recover dicarboxylic acid esters and alkylene diols therefrom, comprising:
 (a) in a first zone liquefying the solid phase polyester to produce a liquid phase medium containing the polyester and/or lower molecular weight depolymerization products thereof;
 (b) transfer the liquid phase medium from said first zone to a second zone in which elevated pressure conditions prevail; and
 (c) in said second zone reacting the resulting liquid phase medium with an aliphatic monohydric alcohol to effect depolymerization of said polyester and/or said depolymerization products to produce the dicarboxylic acid ester.

* * * * *